United States Patent [19]

Desjardins

[11] Patent Number: 4,816,406
[45] Date of Patent: Mar. 28, 1989

[54] INHIBITION OF TRICHOTHECENE TOXINS BY ANCYMIDOL

[75] Inventor: Anne E. Desjardins, Peoria, Ill.

[73] Assignee: The United States of America, as represented by the Secretary of Agriculture, Washington, D.C.

[21] Appl. No.: 889,069

[22] Filed: Jul. 24, 1986

[51] Int. Cl.$^4$ .......................... C12N 1/14; C12R 1/77; A01N 43/48; A23L 3/34
[52] U.S. Cl. .................................... 435/254; 435/929; 426/321; 426/331; 426/419; 514/258
[58] Field of Search ............... 435/243, 245, 254, 929, 435/945; 426/61, 331, 335, 419, 321; 514/258, 269

[56] References Cited

PUBLICATIONS

Coolbaugh et al., *Plant Physiol.* 62: 571–576 (1978).
P. Leroux et al., "Resistance to Fungicides which Inhibit Ergosterol Biosynthesis on Laboratory Strains of *Botrytis Cinerea* and *Ustilago Maydis*", Pestic. Sci. 15: 85–89 (1984).
J. B. Shive, Jr. et al., "Effects of Ancymidol (A Growth Retardant) and Triarimol (A Fungicide) on the Growth, Sterols, and Gibberellins of Phaseolus Vulgaris (L.)", Plant Physiol. 57: 640–644 (1976).
A. Ali et al., "Inhibition of Fungal Growth by Plant Growth Retardants", Notes, Can J. Bot. 57: 458–460 (1979).
R. C. Coolbaugh et al. "Comparative Effects of Substituted Pyrimidines on Growth and Gibberellin Biosynthesis in *Gibberella Fujikuroi*", Plant Physiol. 69: 712–716 (1982).

Primary Examiner—Elizabeth C. Weimar
Attorney, Agent, or Firm—M. Howard Silverstein; David G. McConnell; Curtis P. Ribando

[57] ABSTRACT

The compound ancymidol, a known potent plant growth retardant and weak fungicide, has now been found to inhibit biosynthesis of trichothecene toxins on substrates susceptible to growth of trichothecene-producing fungi. These fungi are known to contaminate cereal grains, forage crops, and potatoes. The effective level of ancymidol addition for toxin inibition is substantially less than that required for control of fungal growth.

9 Claims, No Drawings

INHIBITION OF TRICHOTHECENE TOXINS BY ANCYMIDOL

BACKGROUND OF THE INVENTION

1. Field of the Invention

Trichothecenes are a closely related group of biologically active secondary metabolites produced by certain species of Fusarium and by related fungal genera in the class Hyphomycetes. Production of the toxins in agricultural commodities has led to a variety of mycotoxicoses in man and animal. The Fusaria occur widely in nature on many hosts and substrates and are among the most common of all the fungi.

It is well established that the trichothecene skeleton is formed by mevalonate via farnesyl pyrophosphate and trichodiene [Ciegler, J. Food Protec. 42: 825–828 (1979)]. All toxic trichothecenes possess a 12,13-epoxy-Δ9 nucleus, which is believed to be formed via oxygenation of trichodiene. Desjardins et al. [Appl. Environ. Microbiol. 51: 493–497 (1986)] have shown that the oxygens of the pyran nucleus, the 12,13-epoxide, and the various hydroxyl groups are all derived from molecular oxygen. It may be concluded that these six oxygenations are catalyzed by aliphatic hydroxylases which are either dioxygenases or monooxygenases. These enzyme mechanisms can be distinguished by their sensitivity to a variety of inhibitors. In the course of studying the effects of several known and presumptive monooxygenase inhibitors and analogous compounds on trichothecene biosynthesis in *Fusarium sporotrichioides*, which produces T-2 toxin as the end product, and *Fusarium sambucinum*, which produces diacetoxyscirpenol as the end product, I have arrived at the subject invention.

2. Description of the Prior Art

One such inhibitor I have investigated is ancymidol. Ancymidol has been reported in the literature as having plant growth regulator activity at concentrations less than $10^{-6}$ M (0.2 μg./ml.). Inhibition of plant growth by ancymidol was first demonstrated by Tschabold et al. [Plant Physiol. 46: 19 (1970)]. Leopold [Plant Physiol. 48: 537–540 (1971)] and Shive and Sisler [Plant Physiol. 57: 640–644 (1976)] determined that gibberellin relieved the growth retardation by ancymidol in lettuce hypocotyls, green bean plants, and corn seedlings. Coolbaugh et al. [Plant Physiol. 57: 245–248 (1976) and Plant Physiol. 69: 707–711 (1982)] found that ancymidol blocked three oxidative reactions in the gibberellin biosynthetic pathway in higher plants.

Ancymidol is also weakly fungitoxic. Shive and Sisler, supra, found ancymidol at 100 μg./ml. to inhibit dry weight increase of *Gibberella fujikuroi* by 23%. However, no concentration was found where dry weight was not affected and gibberellin activity produced was affected. Ali [Can. J. Bot. 57: 458–460 (1979)] showed ancymidol at 4 μg./ml. to inhibit radial growth of *Fusarium graminearum* by 50%. Coolbaugh et al. [Plant Physiol. 69: 712–716 (1982)] found ancymidol at $10^{-3}$ M (250 μg./ml.) to inhibit dry weight increase of *Gibberella fujikuroi* by 88%. They also showed that ancymidol was much less effective in inhibiting gibberellin biosynthesis in the fungus than in higher plants. Effects of ancymidol on other fungal enzyme systems were not studied.

SUMMARY OF THE INVENTION

I have now discovered that the compound ancymidol inhibits the biosynthesis of trichothecene toxins on substrates susceptible to growth of tricothecene-producing fungal species when the compound is applied to the substrate in amounts substantially less than that needed to block fungal growth itself.

In accordance with this discovery, it is an object of the invention to define a previously unrecognized trichothecene toxin control agent.

It is also an object of the invention to provide a new and unobvious use for ancymidol.

It is a further object of the invention to control trichothecene toxins in cereal grains and other crops by addition of extremely low levels of ancymidol safe for human and animal consumption.

Other objects and advantages of this invention will become readily apparent from the ensuing description.

DETAILED DESCRIPTION OF THE INVENTION

The name "ancymidol" is generic for α-cyclopropyl-α-(p-methoxyphenyl)-5-pyrimidinemethanol and identifies the compound represented by the structural formula I, below.

Ancymidol

Pure ancymidol is characterized as a white crystalline solid having a melting point of 110°–111° C. Ancymidol is freely soluble in DMSO, acetone, methanol, chloroform, and other polar solvents; moderately soluble in aromatic hydrocarbons such as benzene; and only slightly soluble in saturated hydrocarbon solvents. In water it is soluble at levels of approximately 650 p.p.m. at 25° C.

Ancymidol is relatively nontoxic as indicated by oral feeding studies over a 3-month period with rats and dogs. In the studies, all test animals survived without significant changes at 8000 p.p.m. of the feed, corresponding to a dose in the dogs of 20 mg./kg. body weight ("Technical Report on 'A-REST'," Lilly Research Laboratories).

In accordance with the objective of the invention, it is envisioned that ancymidol may be applied to any liquid or solid substrate susceptible to contamination with trichothecenes. As secondary fungal metabolites, the toxins are associated with the senescent fungus. All substrates susceptible to growth of the fungus are therefore targets for treatment. Of particular interest are cereal grains, forage crops, and potatoes, especially those which are stored for extended periods. It is sufficient to commence treatment at any time during the primary phase of fungal growth. However, as a practical matter, it would be efficacious to treat the grain or other crop material at the time of storage.

Ancymidol may be formulated with one of the aforementioned solvents or with any suitable carrier or vehicle as known in the art. Solutions of ancymidol in DMSO are readily miscible with water. The compound is unstable under acidic conditions, and it is therefore important to maintain the formulation at pH 4 or greater. The ancymidol formulation may be sprayed onto the substrate or otherwise applied by any conventional means.

In accordance with this invention, ancymidol finds utility in virtually all fungal systems known to produce trichothecenes. Included in this category, without limitation, are species of *Fusarium, Acremonium, Trichoderma, Trichothecium, Myrothecium, and Stachybotrys,* all belonging to the class Hyphomycetes. The end product of the trichothecene biosynthetic pathway may vary from species to species. It is now known that blockage of only the end product in the natural pathway will lead to accumulation of other trichothecene toxins which are otherwise intermediates to the end product. However, of those species studied, all produce trichothecenes via the nontoxic, trichodiene intermedite. I have discovered that ancymidol blocks the epoxidation of trichodiene, presumably by inhibition of the cytochrome P-450 monooxygenase. Thus, biosyntheses of all trichothecene intermediates and end products are blocked.

The principal advantage of this invention relates to the specificity of ancymidol when applied at the proper rate to a substrate susceptible to contamination by trichothecene toxins. On a given substrate the effective amount of ancymidol required for trichothecene inhibition is consistently at least one or two orders of magnitude less than that required to achieve a comparable degree of fungal growth inhibition. The expression "specific effective amount" is defined herein to mean that amount of ancymidol which will achieve the desired response in terms of trichothecene inhibition without substantial inhibition of fungal growth. The actual amount will vary depending upon the substrate, the specific fungal organism, the level of fungal contamination, and the conditions of growth. Typically, by application of a specific effective amount of ancymidol, it will be possible to inhibit 50-100% of the toxin production.

The following examples are intended only to further illustrate the invention and are not intended to limit the scope of the invention which is defined by the claims.

EXAMPLES 1-2

*Inhibitor Screening Experiment. Fusarium sambucinum* isolate R-6380 (Pennsylvania State University Fusarium Research Center) was grown on "V-8" juice agar. Conidial suspensions were prepared and frozen in 50% v/v glycerol at −90° C. A 2800-ml. Fernback flask containing 1 liter of 5% glucose, 0.1% peptone, and 0.1% yeast extract was inoculated with thawed conidia to a final concentration of 105 per ml. The culture was incubated at 28° C. in the dark on a gyrotory shaker at 200 r.p.m. After 24 hours, 10-ml. aliquots were removed to measure dry weight and toxin levels. Twenty-five ml. volumes of the culture were transferred to 50-ml. Erlenmeyer flasks with metal caps. Twenty-three test compounds to be screened were added to the cultures in DMSO to a final concentration of 1% v/v. All compounds were tested in duplicate cultures. At 48 hrs., the test compounds were again added to the cultures. Incubation as above continued for a total of 5 days, at which time 5-ml. aliquots were collected to measure dry weight. Total cultures were extracted twice with 25 ml. ethylacetate and evaporated to dryness. The residue was dissolved in acetonitrile-water (9:1), applied to a charcoal cleanup column, eluted with acetonitrile-water, and evaporated to dryness. The residue was dissolved in toluene:acetone:methanol (2:1:1), evaporated to dryness under nitrogen, derivatized with "TBT" (Pierce Chemical Co.), diluted in hexane, and analyzed for diacetoxyscirpenol using a Spectro-Physics gas chromatograph.

The results of the ancymidol assay are reported in Table I, below. Data are expressed as follows: net fungal growth was determined by subtracting the dry weight at 24 hrs. from the dry weight at 5 days, and normalized by dividing by net growth of the DMSO-treated control. Net diacetoxyscirpenol production was determined by subtracting diacetoxyscirpenol at 24 hrs. from toxin at 5 days and normalized by dividing by the net toxin of the DMSO-treated control.

EXAMPLE 3

The procedure of Examples 1-2 was repeated except that at 24 hrs. after inoculation, ancymidol was added to a final concetration of 1 mM to the 1-liter culture. After extracting the culture four times with 500 ml. ethylacetate and evaporating to dryness, the sample was redissolved in ethylacetate and analyzed by GC-MS. The hydrocarbon in the sample was determined, by comparison to an authentic standard, to be trichodiene. This experiment established that no significant amounts of epoxide intermediates or end products were produced by the fungus in the presence of ancymidol.

TABLE I

Effects of Ancymidol on *F. sambucinum*

| Example | Ancymidol level (mM) | Net fungal growth (% of controls)[a] | Net DAS[b] production (% of control)[a] |
|---|---|---|---|
| 1 | 2 | 62 | 3 |
| 2 | 0.2 | 74 | 13 |

[a]Values represent average of duplicate cultures.
[b]DAS = diacetoxysciropenol.

EXAMPLES 4-8

*The Effect of Ancymidol on Trichothecene Biosynthesis in Rice. F. sambucinum* R-6380 (Pennsylvania State University Fusarium Research Center) was used for this study. The inoculum was a conidial suspension obtained by washing the surface of 1-week old "V-8" grown cultures with sterile distilled water. Five ml. of inoculum at $3 \times 10^{-7}$ conidia per ml. were added to each 300-ml. Erlenmeyer flask containing 30 g. rice autoclaved with 13 ml. water. The cultures were incubated at 28° in the dark for 4 days, at which time the rice was evenly colonized. Ancymidol was added to the cultures as 100-mM solution in DMSO. After 10 days further incubation, the cultures were extracted three times by homogenization with 100 ml. ethylacetate. The ethylacetate extract was concentrated and analyzed by GC/MS. The results are reported in Table II, below.

EXAMPLES 9-12

*Fungicide Screening Protocol.* Each of two strains of *F. sambucinum* and *F. sporotrichioides* was grown on "V-8" juice agar. Conidial suspensions were prepared by washing the surface of a 1-week old culture with sterile distilled water. A 300-ml. flask, containing 150 ml. of 5% glucose, 0.1% peptone, and 0.1% yeast extract was inoculated with conidia of each strain to a final concentration of 105 per ml. The culture was incubated at 28° C. in the dark on a gyrotory shaker at 200 r.p.m. After 24 hrs., 10-ml. aliquots were removed to measure dry weight and toxin levels. Twenty-five ml. volumes of the culture were transferred to 50-ml. Erlenmeyer flasks with metal caps. Ancymidol was added to duplicate cultures in DMSO (to a final concetration of 1% v/v). At 48 hrs., ancymidol was again added to the culture such that the final concentration of ancymidol was 2 mM. Incubation as above continued for a total of 7 days, at which time 5-ml. aliquots were collected to measure dry weight. Total cultures were extracted twice with 25 ml. ethylacetate and evaporated to dryness. The residue was dissolved in 1 ml. ethylacetate and analyzed by GC/MS.

TABLE II

| Example | Ancymidol (μmoles/g. rice) | Diacetoxyscirpenol (μg./g. rice)[a] |
|---|---|---|
| 4 | 0 | 252 |
| 5 | 0.33 | 160 |
| 6 | 1.0 | 140 |
| 7 | 2.0 | 143 |
| 8 | 3.3 | 143 |

Diacetoxysciropenol in Ancymidol-Treated Cultures of F. sambucinum on Rice

[a]Values represent average of duplicate cultures.

The results are reported in Table III, below. Data are expressed as follows: net growth was determined by subtracting the dry weight at 24 hrs. from the dry weight at 7 days, and normalized by dividing by net growth of the DMSO-treated control. Net toxin production was determined by subtracting toxin at 24 hrs. from toxin at 7 days and normalized by dividing by net toxin of the DMSO-treated control.

EXAMPLES 13-22

F. sambucinum isolate R-6380 (Pennsylvania State University Fusarium Research Center) was grown on "V-8" juice agar. A conidial suspension was prepared by washing the surface of a 1-week-old culture with sterile distilled water. A 2800-ml. Fernbach flask containing 750 ml. of 5% glucose, 0.1% peptone, and 0.1% yeast extract was inoculated with conidia to a final concentration of 105 per ml. The culture was incubated at 28° C. in the dark on a gyrotory shaker at 200 r.p.m. After 24 hrs., 10-ml. aliquots were removed to measure dry weight and toxin levels. Twenty-five ml. volumes of the culture were transferred to 50-ml. Erlenmeyer flasks with metal caps. Ancymidol was added to duplicate cultures according to the regime set forth in Table IV. Incubation as above continued for a total of 7 days, at which time 5-ml. aliquots were collected to measure dry weight. Total cultures were extracted twice with 25 ml. ethylacetate and evaporated to dryness. The residue was dissolved in 1 ml. ethylacetate and analyzed by GC/MS.

Diacetoxyscirpenol production was determined by dividing toxin at 7 days by toxin of the DMSO-treated control at 7 days. The results are reported in Table IV, below.

EXAMPLES 23-30

Fusarium sporotrichioides strain 3299 was grown on "V-8" juice agar. Conidial suspensions were prepared by washing the surface of a 1-week-old culture with sterile distilled water. A 50-ml. flask containing 25 ml. of 5% glucose, 0.1% peptone, and 0.1% yeast extract was inoculated with

TABLE III

Effects of Ancymidol on F. sporotrichioides and F. sambucinum

| Example | Fungus | Net fungal growth as % of DMSO-treated control[a] | Net toxin as % of DMSO-treated control[a] | |
|---|---|---|---|---|
| | | | DAS[b] | T-2 |
| 9 | Fusarium sporotrichioides strain #3299 | 51 | — | 0 |
| 10 | F. sporotrichioides strain #MB 1716[c] | 57 | 14 | — |
| 11 | F. sambucinum strain #6380 | 54 | 3 | — |
| 12 | F. sambucinum strain #278-34 | 63 | 0 | — |

[a]Values represent average of duplicate cultures.
[b]DAS = diacetoxyscirpenol.
[c]This UV-induced mutant makes only diacetoxyscirpenol.

TABLE IV

Effect of Ancymidol on Diacetoxyscirpenol (DAS) Production by F. sambucinum

| Example | Ancymidol addition (mM) | | | | | DAS at day 7 as % of DMSO-treated control | Net DAS toxin as % of DMSO-treated control[a] |
|---|---|---|---|---|---|---|---|
| | Day 1 | Day 2 | Day 3 | Day 4 | Day 5 | | |
| 13 (DMSO control) | 0 | 0 | 0 | 0 | 0 | 100 | — |
| 14 | 1 | 1 | 0 | 0 | 0 | 10 | 3 |
| 15 | 2 | 0 | 0 | 0 | 0 | 13 | 6 |
| 16 | 1 | 1 | 1 | 0 | 0 | 14 | 7 |
| 17 | 0 | 1 | 1 | 0 | 0 | 61 | 0 |
| 18 | 0 | 2 | 0 | 0 | 0 | 58 | 0 |
| 19 | 0 | 1 | 1 | 1 | 0 | 55 | 0 |
| 20 | 0 | 0 | 1 | 1 | 0 | 103 | 33 |
| 21 | 0 | 0 | 2 | 0 | 0 | 89 | 19 |
| 22 | 0 | 0 | 1 | 1 | 1 | 76 | 6 |

[a]Computed as the toxin at day 7 minus the toxin level prior to the first treatment with ancymidol.

conidia to a final concentration of 105 per ml. The cultures were incubated at 28° C. in the dark on a gyrotory shaker at 200 r.p.m. At 24 hrs., ancymidol was added to duplicate cultures in DMSO to a final concentration of 1% v/v. At 48 hrs., ancymidol was again added to the cultures such that the final concentration was as indicated in Table V. Incubation as above continued for a total of 7 days, at which time 5-ml. aliquots were collected to measure dry weight. T-2 in culture filtrates was assayed using monoclonal antibodies.

Net growth was determined by subtracting the dry weight at 24 hrs. from the dry weight at 7 days, and normalized by dividing by net growth of the DMSO-treated control. Net T-2 was determined by subtracting T-2 at 24 hrs. from T-2 at 7 days and normalized by dividing by net T-2 of the DMSO-treated control.

It is understood that the foregoing detailed description is given merely by way of illustration and that modifications and variations may be made therein without departing from the spirit and scope of the invention.

TABLE V

Dose Response of Fungal Growth and T-2 Toxin to Ancymidol in *F. sporotrichioides*

| Example | Ancymidol (mM) | Net fungal growth as % of DMSO-treated control[a] | Net T-2 toxin as % of DMSO-treated control[a,b] |
|---|---|---|---|
| 23 | 2 | 87 | 20 |
| 24 | 1 | 90 | 21 |
| 25 | 0.2 | 97 | 38 |
| 26 | 0.1 | 95 | 57 |
| 27 | 0.02 | 98 | 73 |
| 28 | 0.01 | 99 | 85 |
| 29 | 0.002 | 100 | 90 |
| 30 | 0.001 | 97 | 100 |

[a]Values represent average of quadruplicate cultures.
[b]T-2 of control = 90 μg./ml.

I claim:
1. A method of protecting a substrate susceptible to growth of a trichothecene-producing fungus against contamination by trichothecene toxins comprising applying to said substrate ancymidol in a specific effective amount to inhibit biosynthesis of said toxins.
2. The method of claim 1 wherein said fungus is a Fusarium species.
3. The method of claim 2 wherein said Fusarium is *Fusarium sporotrichioides*.
4. The method of claim 2 wherein said Fusarium is *Fusarium sambucinum*.
5. The method of claim 1 wherein said substrate is stored grain.
6. The method of claim 5 wherein said substrate is corn.
7. The method of claim 5 wherein said substrate is rice.
8. The method of claim 1 wherein said substrate is a stored forage crop.
9. The method of claim 1 wherein said substrate is stored potatoes.

* * * * *